US005780694A

United States Patent [19]

Singleton

[11] Patent Number: 5,780,694
[45] Date of Patent: Jul. 14, 1998

[54] DIMERIZED ALCOHOL COMPOSITIONS AND BIODEGRADIBLE SURFACTANTS MADE THEREFROM HAVING COLD WATER DETERGENCY

[75] Inventor: David M. Singleton. Houston. Tex.

[73] Assignee: Shell Oil Company. Houston. Tex.

[21] Appl. No.: 755,827

[22] Filed: Nov. 26, 1996

[51] Int. Cl.$^6$ ................................................. C07C 27/20
[52] U.S. Cl. ........................................ 568/909; 585/512
[58] Field of Search ............................ 568/909; 585/512

[56] References Cited

U.S. PATENT DOCUMENTS

| | | | |
|---|---|---|---|
| 3,004,087 | 10/1961 | Goddard et al. | 585/512 |
| 3,231,621 | 1/1966 | Slaugh | 260/604 |
| 3,239,566 | 3/1966 | Slaugh et al. | 260/604 |
| 3,239,569 | 3/1966 | Slaugh et al. | 260/632 |
| 3,239,570 | 3/1966 | Slaugh et al. | 260/632 |
| 3,239,571 | 3/1966 | Slaugh et al. | 260/632 |
| 3,420,898 | 1/1969 | Van Winkle et al. | 260/632 |
| 3,424,815 | 1/1969 | Cannell et al. | 260/683.15 |
| 3,440,291 | 4/1969 | Van Winkle et al. | 260/632 |
| 3,448,157 | 6/1969 | Slaugh et al. | 260/604 |
| 3,448,158 | 6/1969 | Slaugh et al. | 260/604 |
| 3,496,203 | 2/1970 | Morris et al. | 260/439 |
| 3,496,204 | 2/1970 | Morris et al. | 260/439 |
| 3,501,515 | 3/1970 | Van Winkle et al. | 260/439 |
| 3,527,818 | 9/1970 | Mason et al. | 260/632 |
| 3,636,034 | 1/1972 | Ohsumi et al. | 260/459 |
| 3,843,706 | 10/1974 | Weil et al. | 260/458 |
| 3,931,271 | 1/1976 | Baumann et al. | 260/458 |
| 3,952,068 | 4/1976 | Gipson et al. | 260/632 R |
| 4,320,237 | 3/1982 | Kaufold et al. | 568/909 |
| 4,474,678 | 10/1984 | Lutz et al. | 252/174.21 |
| 4,721,816 | 1/1988 | Edwards | 568/618 |
| 4,959,491 | 9/1990 | Threlkel | 562/94 |
| 5,026,933 | 6/1991 | Blain et al. | 585/7 |
| 5,112,519 | 5/1992 | Giacobbe et al. | 252/174.21 |
| 5,196,625 | 3/1993 | Threlkel et al. | 585/513 |
| 5,389,277 | 2/1995 | Prieto | 252/99 |
| 5,414,160 | 5/1995 | Sato et al. | 568/883 |
| 5,446,213 | 8/1995 | Sato et al. | 568/883 |
| 5,468,419 | 11/1995 | Miyazawa et al. | 252/182.12 |
| 5,510,306 | 4/1996 | Murray | 502/64 |

FOREIGN PATENT DOCUMENTS

| | | |
|---|---|---|
| 0329670 | 10/1987 | European Pat. Off. . |
| 0300444 | 7/1988 | European Pat. Off. . |
| 0373850 | 12/1989 | European Pat. Off. . |
| 0439316 | 1/1991 | European Pat. Off. . |
| 01160928 A | 6/1989 | Japan . |
| 04036251 A2 | 2/1992 | Japan . |
| WO 95/21225 | 8/1995 | WIPO . |

OTHER PUBLICATIONS

"Atlas of Zeolite Structure Types" by W. M. Meier and D. H. Olson. published on behalf of the Structure Commission of the International Zeolite Association, May 24, 1989, pp. 4–10, 134–135, 106–107, and 64–65.

*Primary Examiner*—Ceila Chang
*Assistant Examiner*—Garth M. Dahlen
*Attorney, Agent, or Firm*—Dennis V. Carmen

[57] ABSTRACT

There is provided an alcohol composition obtained by dimerizing an olefin feed comprising $C_6$–$C_{10}$ linear olefins to obtain $C_{12}$–$C_{20}$ olefins, followed by conversion to alcohols, such as by hydroformylation. The composition has an average number of branches ranging from 0.9 to 2.0 per molecule. The linear olefin feed preferably comprises at least 85% of $C_6$–$C_8$-olefins. The primary alcohol compositions are then converted to anionic or nonionic surfactants, preferably sulfated or oxyalkylated or both. The sulfated compositions are biodegradable and possess good cold water detergency. The process for making the dimerized primary alcohol comprises dimerizing, in the presence of a homogeneous dimerization catalyst under dimerization conditions, an olefin feed comprising $C_6$–$C_{10}$ olefins and preferably at least 85 weight % of linear olefins based on the weight of the olefin feed, to obtain a $C_{12}$–$C_{20}$; optionally double bond isomerizing said $C_{12}$–$C_{20}$ olefins; and converting the $C_{12}$–$C_{20}$ olefins to alcohols, preferably through hydroformylation. The process is preferably a one-step dimerization. The homogenous catalyst comprises a mixture of a nickel carboxylate or a nickel chelate, with an alkyl aluminum halide or an alkyl aluminum alkoxide.

23 Claims, No Drawings

5,780,694

DIMERIZED ALCOHOL COMPOSITIONS AND BIODEGRADIBLE SURFACTANTS MADE THEREFROM HAVING COLD WATER DETERGENCY

FIELD OF THE INVENTION

The invention pertains to a primary alcohol composition and the sulfates thereof simultaneously exhibiting improved cold water detergency and ready biodegradability. In particular, the invention relates to a branched primary alcohol composition having an average number of branches of 0.9 to 2.0, made by dimerizing a $C_6$–$C_{10}$ feed of linear olefins, and subsequently converting the resultant $C_{12-20}$ branched dimerized olefins to a primary alcohol composition, followed by sulfation where a detergent is desired.

BACKGROUND OF THE INVENTION

The alcohols of long chain olefins having about 12 to 20 carbon atoms have considerable commercial importance in a variety of applications, including detergents, soaps, surfactants, and freeze point depressants in lubricating oils. These alcohols are produced by any one of commercial processes, such as the oxo or hydroformylation of long chain olefins. Typical long chain alcohols are the commercially available NEODOL® alcohols made by Shell Chemical Company, the EXXAL® alcohols available from Exxon Chemical, and the LIAL® alcohols available from Enichem.

In the manufacture of the NEODOL® alcohols, a predominantly linear olefin feed is subjected to hydroformylation by reacting carbon monoxide and hydrogen onto the olefin in the presence of an Oxo catalyst to form an alcohol. In excess of 80% of the number of alcohol molecules in the resultant alcohol composition are linear primary alcohols. Of the branched primary alcohols in the composition, substantially all, if not all, of the branching is on the $C_2$ carbon atom relative to the hydroxyl bearing carbon atom. These alcohols can subsequently be converted to anionic or nonionic detergents or general surfactants by sulfonation or ethoxylation, respectively, of the alcohol. Also known as anionic surfactants for detergents are the alcoholethoxysulfates.

The NEODOL® line of alcohols have met with considerable commercial success as detergent precursors because the NEODOL® alcohol compositions can be economically produced with high yields of linear alcohols. The desire to use linear alcohols as intermediates for detergent grade surfactants exists because it is generally recognized that linear alcohols biodegrade, while the branched long chain alcohol sulfonates exhibit poor biodegradability. Since detergents and soaps used by consumers for washing are ultimately released into the environment, the need to provide a surfactant or detergent which biodegrades is well recognized.

For example, U.S. Pat. No. 5,112,519 describes the manufacture of a surfactant by oligomerizing $C_3$ and $C_4$ olefins through a surface deactivated ZSM-23 catalyst to form oligomers, hydroformylating the oligomer, and recovering a semi-linear alcohol composition having less than 1.4 methyl branches, and whose branching is limited to methyl branches. The alcohol can be ethoxylated and/or sulfated and is reported to be biodegradable, and further have improved low temperature properties compared to isotridecyl alcohol. Retaining the linearity of the alcohol composition to less than 1.4, along with obtaining methyl branching were important considerations to achieving a biodegradable surfactant. It would be desirable, however, to obtain a biodegradable surfactant without limiting the branching to methyl branches, without limiting the branching to under 1.4, and without limiting oneself to a ZSM 23 surface deactivated catalyst. It would also be desirable to make a biodegradable surfactant without conducting oligomerization reactions through zeolite catalysts, which are expensive and may coke up or be used up quickly if one needs to build chain length through the catalyst.

Another product, EXXAL® 13, is derived from propylene oligomerization through acid catalysis to a wide range of mono-olefins, the range having an average of C13s being distilled out, but containing some olefins in the $C_{10-15}$ range. The olefin is then subjected to hydroformylation using an oxo process. EXXAL® 13 is reported to be a 3–4 methyl branched tridecyl-alcohol known for its use in lubricants and in those detergent formulations which do not require rapid biodegradation. This is because EXXAL® 13 only slowly biodegrades. While such a high amount of branching is not necessary, it would be desirable to make a surfactant having a high amount of branching for detergency which is nevertheless readily biodegradable.

The dimerization of low carbon numbered olefins is generally known in the Dimersol® process. This process is a catalyzed liquid phase oligomerization, primarily dimerization, of propylene or butylene. The process was developed by the Institute Francais du Petrole. The process uses generally a catalyst prepared by reacting a nickel compound with a hydrocarbyl aluminum halide. The primary product is the dimer of the propylene or butylene with smaller amounts of the trimer and tetramer being present. General discussion of the Dimersol Process can be found in Hydrocarbon Processing, Vol.89, pp 143–149, May, 1980 and Vol. 91, pp 110–112, May, 1982.

U.S. Pat. No. 4,584,411 reports that higher oligomers made from proplyene and butylene, i.e., the small quantities of trimers and tetramers forming up to $C_{12}$ oligomerized olefins, are fractionated out of the dimerized stream composed mainly of $C_{6-8}$ dimerized olefins, and then subjected to conversion to alcohols as intermediates in detergents and lubricant products. However, the dimerized stream was first treated with a tantalum (V) halide/oxide-inorganic oxide catalyst for the purpose of oligomerizing out the more highly branched materials, thereby producing a linear product which was hydroformylated. It was recognized that the oligomerization process produced branched materials, which were reported to be undesirable, and hence, treated. It would be desirable, however, to utilize a process in which one is not reliant on using a proplyene or butylene feed prior to dimerization, which produces primarily only $C_6$ or 8 dimerized olefins, and which does not rely upon utilizing minor quantities of trimers and tetramers which may contain quaternary carbon atoms, and which can form both odd and even numbered olefins, and which, contrary to the direction of the teachings in U.S. Pat. No. 4,584,411, form highly branched primary alcohol compositions which are biodegradible.

Similarly, U.S. Pat. No. 4,959,491 reports that $C_{12}$ olefins can be manufactured in a two step dimerization process by dimerizing propylene, fractionally distilling out about 70 to 82% of linear $C_6$ dimer product (special extraction steps must be used to obtain a higher purity of linearity), and subjecting the product again to dimerization to produce a semi-linear $C_{12}$ olefin comprised of a mixture of linear and mono-branched olefin. These products are then reacted with benzene and sulfated to produce biodegradable alkylbenzene sulfonates. No mention is made of the suitability of these types of olefins for the manufacture of primary alcohol compositions. Further, as noted above, it would be desirable to manufacture an high carbon chain olefin without limitation to dimerizing propylene, and without the necessity for utilizing multiple dimerization steps. It would also be desirable to make primary alcohol compositions having a higher number of branches than what one would expect with a mixture of linear and mono-branched olefins.

U.S. Pat. No. 5,196,625 describes a dimerization process for producing linear and/or mono -branched C10 to C28 olefins using dimerization catalysts, for the production of biodegradable alkylbenzene sulfonates detergents by alkylating the olefins onto benzene. While this patent reports the use of a $C_5$ to $C_{10}$ feed of olefins, no mention is made of using the dimerized olefins to make alcohols. Further, the patentee reported that it is generally recognized that "linear and mono-branched alkyl aromatic sulfonates are generally much more readily biodegraded than multibranched alkyl aromatic sulfonates and, hence, much more desirable as detergents." The patentee sought to ensure that the olefins made were substantially linear and monobranched to avoid sacrificing biodegradibility. However, we have found it desirable to make highly branched alcohols to improve cold water detergency of detergent alcohol sulfates.

There exists a growing need to find alcohol intermediates for the manufacture of sulfate detergents which are both biodegradable and exhibit good detergency at cold wash temperatures, that is, increasing branching which we have found to increase cold water detergency, but without sacrificing ready biodegradibility. The process employed should be simple and flexible enough to produce a wide variety of products.

SUMMARY OF THE INVENTION

There is now provided an alcohol composition obtained by dimerizing an olefin feed comprising $C_6$–$C_{10}$ linear olefins to obtain $C_{12}$–$C_{20}$ olefins, followed by conversion to alcohols, such as by hydroformylation. The composition has an average number of branches ranging from 0.9 to 2.0 per molecule. The linear olefin feed preferably comprises at least 85% of $C_6$–$C_8$-olefins. The primary alcohol compositions are then converted to anionic or nonionic surfactants, preferably sulfated or oxyalkylated or both. The sulfated compositions are biodegradable and possess good cold water detergency.

The process for making the dimerized primary alcohol comprises dimerizing, in the presence of a homogeneous dimerization catalyst under dimerization conditions, an olefin feed comprising $C_6$–$C_{10}$ olefins and preferably at least 85 weight % of linear olefins based on the weight of the olefin feed, to obtain a $C_{12}$–$C_{20}$; optionally double bond isomerizing said $C_{12}$–$C_{20}$ olefins; and converting the $C_{12}$–$C_{20}$ olefins to alcohols, preferably through hydroformylation. The process is preferably a one-step dimerization. The homogenous catalyst comprises a mixture of a nickel carboxylate or a nickel chelate, with an alkyl aluminum halide or an alkyl aluminum alkoxide.

DETAILED DESCRIPTION OF THE INVENTION

The present invention provides for the dimerization of $C_6$–$C_{10}$ olefins, their conversion to alcohols, and their subsequent use as surfactants which are biodegradable and have good cold water detergency.

As used herein, the phrase average number of branches per molecule chain refers to the average number of branches per alcohol molecule, as measured by $^{13}C$ Nuclear Magnetic Resonance ($^{13}C$ NMR ) as discussed below. The average number of carbon atoms in the chain are determined by gas chromatography mass spectrometry (GCMS).

Various references will be made throughout this specification and the claims to the percentage of branching at a given carbon position, the percentage of branching based on types of branches, average number of branches, and percentage of quaternary atoms. These amounts are to be measured and determined by using a combination of the following three $^{13}C$-NMR techniques. (1) The first is the standard inverse gated technique using a 45-degree tip $^{13}C$ pulse and 10 s recycle delay (an organic free radical relaxation agent is added to the solution of the branched alcohol in deuterated chloroform to ensure quantitative results). (2) The second is a J-Modulated Spin Echo NMR technique (JMSE) using a 1/J delay of 8 ms (J is the 125 Hz coupling constant between carbon and proton for these aliphatic alcohols). This sequence distinguishes carbons with an odd number of protons from those bearing an even number of protons, i.e. $CH_3/CH$ vs $CH_2/C_q$ ($C_q$ refers to a quaternary carbon). (3) The third is the JMSE NMR "quat-only" technique using a ½J delay of 4 ms which yields a spectrum that contains signals from quaternary carbons only. The JSME NMR quat only technique for detecting quaternary carbon atoms is sensitive enough to detect the presence of as little at 0.3 atom % of quaternary carbon atoms. As an optional further step, if one desires to confirm a conclusion reached from the results of a quat only JSME NMR spectrum, one may also run a DEPT-135 NMR sequence. We have found that the DEPT-135 NMR sequence is very helpful in differentiating true quaternary carbons from breakthrough protonated carbons. This is due to the fact that the DEPT-135 sequence produces the "opposite" spectrum to that of the JMSE "quat-only" experiment. Whereas the latter nulls all signals except for quaternary carbons, the DEPT-135 nulls exclusively quaternary carbons. The combination of the two spectra is therefore very useful in spotting non quaternary carbons in the JMSE "quat-only" spectrum. When referring to the presence or absence of quaternary carbon atoms throughout this specification, however, we mean that the given amount or absence of the quaternary carbon is as measured by the quat only JSME NMR method. If one optionally desires to confirm the results, then also using the DEPT-135 technique to confirm the presence and amount of a quaternary carbon.

The detergency evaluations conducted and as used throughout were based from a standard high density laundry powder (HDLP) Detergency/Soil Redeposition Performance test. The evaluations in the working examples were conducted using Shell Chemical Company's radiotracer techniques at the designated temperatures in Table III at a water hardness of 150 ppm as $CaCO_3$ ($CaCl_2/MgCl_2=3/2$ on a molar basis). The primary alcohol sulfated compositions of the invention were tested, on a ¼ cup basis, against multisebum, cetanesqualane and clay soiled permanent press 65/35 polyester/cotton (PPPE/C) fabric. The HDLP's were tested at 0.74 g/l concentration, containing 27 wt % of the primary alcohol sulfate composition, 46 wt % of builder (zeolite-4A) , and 27 wt % of sodium carbonate.

The composition of the radiolabeled Multisebum Soil was as follows:

| Component | Label | % wt. |
| --- | --- | --- |
| Cetane | 3H | 12.5 |
| Squalane | 3H | 12.5 |
| Trisearin | 3H | 10 |
| Arachis (Peanut) Oil | 3H | 20 |
| Cholesterol | 14C | 7 |
| Octadecanol | 14C | 8.0 |
| Oleic Acid | 14C | 15.0 |
| Stearic Acid | 14C | 15.0 |

A Terg-O-Tometer was used to wash the swatches at 15 minute intervals. The wash conditions were set to measure both cold water detergency at 50° F. and warm water detergency at 90° F. The agitation speed was 100 rpm. Once the 4"×4" radiotracer soiled swatches were washed by the Terg-O-Tometer, they were hand rinsed. The wash and rinse waters were combined for counting to measure sebum soil removal. The swatches were counted to measure clay removal.

For details concerning the detergency methods and radiotracer techniques, reference may be had to B. E. Gordon, H. Roddewig and W. T Shebs, HAOCS, 44:289 (1967), W. T. Shebs and B. E. Gordon, JAOCS, 45:377 (1968), and W. T. Shebs, Radioisotope Techniques in Detergency, Chapter 3, Marcel Dekker, New York (1987), each incorporated herein by reference.

The biodegradation testing methods for measuring the biodegradability of the working example sulfates were conducted in accordance with the test methods established in 40 CFR §796.3200, also known as the OECD 301D test method, incorporated herein by reference. By a biodegradable composition or surfactant is meant that that the compound or composition gives a measured biochemical oxygen demand (BOD) of 60% or more within 28 days, and this level must be reached within 10 days of biodegradation exceeding 10 percent.

The alcohol compositions of the invention are derived from $C_{12}$–$C_{20}$ olefins, preferably from $C_{13-17}$ olefins. This carbon number is where most of the detergent range primary alcohol sulfates lie. The alcohol compositions are generally primary alcohol compositions.

The primary alcohol compositions contain $C_1$–$C_3$ branches connected to one of the dimerized carbons. In some cases, particularly where internal olefins are dimerized, the types of branching at one of the dimerized carbon locations may be a butyl branch. Additionally, the primary alcohol composition may contain a given amount of conjugated branches, meaning that two adjacent carbon atoms on the backbone of the alcohol molecule are branched. Preferably, at least 5 wt. % of the alcohol molecules in the primary alcohol composition are conjugated, more preferably from 10 to 30 wt %.

The primary alcohol composition is highly branched, that is, has an average number of branches ranging from 0.9 to 2.0 per molecule, preferably an average of from about 1 to 1.8 branches, and quite often an average number of branches that is greater than 1. This represents either a monobranched composition with essentially no linear alcohols present, or a mixture of alcohols containing a large number of double branches. In spite of the high number of branches, the primary alcohol sulfates made from the primary alcohol compositions herein are readily biodegradible.

The primary alcohol composition of the invention have relatively few branch points at the $C_1$ through $C_3$ carbon positions relative to the hydroxyl carbon and little or no isopropyl terminations, that is, little or no branches at the second to last carbon atom along the backbone of the alcohol molecule relative to the hydroxyl carbon atom. In particular, the typical alcohol molecule of the invention contains less than 25% branching at the $C_2$ and $C_3$ positions, and less than 5% isopropyl termination, more usually no isopropyl groups being detected.

From these carbon positions, the alcohol molecules of the invention looks similar to the Neodol® alcohols. However, unlike the Neodol® alcohols which are predominately linear, the primary alcohol composition of the invention has a very high average number of branches per molecule. Due to large number of branches found in the primary alcohol composition of the invention and the relatively low percentage of branch points at the $C_2$, $C_3$, and isopropyl terminal carbon positions, the majority of the branches are toward the center of the molecule, with a significant number of the branches being located on one or both of the dimerized carbon atoms. The NMR spectral data is consistent with where the branches are thought to be located based on a chemical reaction equation.

The types of branching found in the primary alcohol composition of the invention varies from methyl, ethyl, propyl, and butyl or higher. A significant number of the branches detected by the NMR were ethyl groups, although this can vary depending upon the composition of the feed and reaction conditions. In one embodiment, however, the number of ethyl groups in the primary alcohol composition of the invention range, preferably, from 10% to 30%, which is a significant jump from the amount of ethyl groups detected in Neodol® alcohols. The number of methyl groups detected by the NMR can also vary widely for the same reason. Typically, however, the number of methyl groups will range from 10% to 50%, as detected by the NMR.

The primary alcohol composition of the invention also preferably has less than 0.5 atom % of $C_q$'s as measured by a quat only JMSE modified $^{13}$C-NMR described above, having a detection limit of 0.3 atom % or better, and preferably an primary alcohol composition which contains no $C_q$'s as measured by this NMR technique. For reasons not yet clearly understood, it is believed that the presence of $C_q$'s on an alcohol molecule prevents the biodegradation of that particular sulfated molecule by biological organisms. An amount of only 1 atom % of $C_q$'s has been found in some alcohols which hardly biodegrade at all. In a preferred embodiment, no quaternary carbon atoms are detected in the primary alcohol composition of the invention.

Broadly speaking, a primary alcohol composition is obtained by dimerizing an olefin feed comprising $C_6$–$C_{10}$ linear olefins in the presence of a dimerization catalyst under dimerization conditions to obtain $C_{12}$–$C_{20}$ olefins, followed by conversion, preferably through hydroformylation, to produce a $C_{13}$–$C_{21}$ primary alcohol composition. The primary alcohol compositions are then sulfated to make surfactants which are biodegradable and possess good cold water detergency.

In one embodiment, the olefin feed comprises at least 85% linear olefins, more preferably at least 90% linear olefins, more preferably at least 95% linear olefins. The remainder of the olefin feed comprises only a small number of branched olefins, preferably less than 3% of branched olefins.

The olefin feed can contain shorter or longer olefins. In a preferred embodiment, however, the olefin stream also comprises at least 85% of the $C_6$–$C_{10}$ olefins, more preferably 90%, and most preferably 95% $C_6$–$C_{10}$ olefins. Another advantage of the process of the invention is that one can take advantage of making mixtures of both odd and even numbered dimerized olefins by employing mixtures of both odd and even numbered olefins in the feed, as distinguished from those processes which rely upon dimerization either $C_3$ or $C_4$ olefins to build higher olefins.

The olefin feed can be made up of internal or alpha olefins, or mixtures thereof. Preferably, the majority of the olefins present in the feed comprise internal olefins because the dimerization of these olefins tend to produce a variety of branch types, that is, methyl, ethyl, and propyl branches, even butyl branches. By a majority is meant that greater than 50 wt % of the olefin feed is comprised of internal olefins. More preferably, at least 75 wt % of the olefin feed is comprised of internal olefins.

Broadly speaking, the process of the invention requires the dimerization of a $C_6$–$C_{10}$ olefin feed, followed by conversion to a primary alcohol composition, as by way of hydroformylation, as noted above. In one embodiment of the invention, there is provided a one-step dimerization process wherein the dimerization of the olefins occurs in only one step. By a one-step dimerization process is meant that an olefin feed, once dimerized, is not further subjected to dimerization. A one-step process does, however, include recycling unreacted olefin feed to the dimerization zone because this unreacted olefin was not dimerized. It also includes a continuous process or several batch reactors operating in parallel, so long as one dimerized stream of olefin is not fed to a subsequent dimerization reaction zone for a second or subsequent dimerization. This one step process provides the advantage that one may use conventional streams of olefins without the necessity for expensive and sophisticated extraction and separation processes for making an olefin stream of high purity linear olefins. The olefin feed may be obtained by the conventional oligomerization of ethylene, which may subsequently be disproportionated, or the Fischer-Tropsch process, which uses a 1 carbon oligomerization by passing CO and H2 over iron or cobalt catalyst; as distinguished from timers or tetramer feeds Of $C_3$ or $C_4$ olefins which are highly branched or require special extraction steps to obtain high linearity in the olefin feed.

Typically, the dimerization is conducted at temperatures in the range of about from about $-10°$ C. to about $100°$ C., preferably from about $20°$ to about $50°$ C. for about ½ to about 8 hours, preferably about 1 to about 5 hours, using an olefin to catalyst mole ratio of about 200 to 20,000, preferably 1,000 to 110,000 moles of olefin per mole of catalyst. The dimerization is generally conducted as a liquid phase reaction using pressures in the range of about 0 to about 3 atmospheres, preferably 1 to 2 atmospheres. Where the dimerization is conducted as a batch process, the catalyst can be conveniently prepared in situ in the reactor. The dimerization can also be conducted as a continuous, semi-batch or multi-step process. It should be appreciated that where typical or preferred process conditions (e.g., temperatures, times, catalyst ratios, etc.) have been given, that other process conditions could also be used. Optimum reaction conditions (e.g., temperature, reaction time, reactant ratios, catalyst ratios, solvents, etc.) may vary with the particular reactants, catalysts, or solvents used, but can be determined by routine optimization procedures.

The dimerization catalysts of this invention can be prepared by contacting the appropriate components of the catalyst in the olefin to be dimerized. Preferably, the components of the catalyst are not mixed together prior to their addition to the olefin feed, as this may cause decomposition of the catalyst. Added solvents, such as chlorobenzene or cyclohexane may be used and do not detract from catalyst performance.

The selection of the catalyst for the dimerization is one which is selective towards the manufacture of high yields of dimerized olefins having and average of from 0.9 to 2.0 branches per molecule. These catalysts are preferably soluble in hydrocarbon media, for example, the olefin feed stream. Examples of dimerization catalysts soluble in hydrocarbons are complexes wherein a metal, preferably nickel, is bound to at least one hydrocarbon group, for example a bis-nickel, a nickel halide or bis-cyclooctadiene nickel associated to a halogenated aluminum compound. Another type of catalyst consists of the complexes formed by admixing at least one nickel compound with at least one alkylaluminum compound and optionally a ligand, for example a phosphine. These catalysts are well-known in the art. Illustrations of the catalyst that can be used in this type of process are given in U.S. Pat. No. 4,366,087; 4,326,650; and 4,398,049, all incorporated by reference herein.

A preferred class of catalysts used in the process are homogenous catalysts comprising a combination of a nickel carboxylate or a nickel chelate, with an alkyl aluminum halide or an alkyl aluminum alkoxide, respectively. The Al/Ni mole ratio is suitably from about 1.0 to about 20.0.

The nickel compound comprises a nickel carboxylate or a nickel chelate. The carboxylate of the nickel carboxylate may be represented by the formula $(RCOO)_2Ni$, where R is a branched or unbranched, hydrocarbyl radical, for example an alkyl, cycloalkyl, alkenyl, aryl, aralkyl or alkaryl radical, containing at least 2 carbon atoms, preferably a sufficient number of carbon atoms to render it compatible with a hydrocarbon media, such as a hydrocarbyl radical of 5–20 carbon atoms, which radical may be substituted with, for example, hydroxy groups. One of the RCOO— groups of the bivalent nickel carboxylate mentioned above may optionally be substituted with a group represented by $R_1COO—$, where $R_1$ is a halogenoalkyl radical containing from 1 to 3 carbon atoms, as described in U.S. Pat. No. 4,366,087.

Examples of the nickel carboxylates include, but are not limited to, bis-(2-ethylhexanoate)nickel; 2-ethylhexanoate nickel trichloro(or trifluoro) acetate; 2-ethylhexanoate nickel o-chlorobenzoate; and 2-ethylhexanoate nickel acetylacetonate, nickel 2-ethylbutyrate trifluoroacetate, nickel 2-ethylbutyrate trichloroacetate, nickel 3,3-dimethylbutyrate trifluoroacetate, nickel 3,3-dimethylbutyrate trichloroacetate, nickel 4-methylvalerate trifluoroacetate, nickel heptanoate trifluoroacetate, nickel heptanoate trichloroacetate, nickel heptanoate tribromoacetate, nickel heptanoate triiodoacetate, nickel 2-ethylhexanoate monofluoroacetate, nickel 2-ethylhexanoate trichloroacetate, nickel 2-ethylhexanoate dichloroacetate, nickel 2-ethylhexanoate monochloroacetate, nickel 2-ethylhexanoate tribromoacetate, nickel 2-ethylhexanoate triiodoacetate, nickel octoate trifluoroacetate, nickel octoate trichloroacetate, nickel decanoate trifluoroacetate, nickel decanoate trichloroacetate, nickel myristate trifluoroacetate, nickel palmitate trifluoroacetate, nickel dodecylbenzoate trifluoroacetate, nickel diisopropylsalicylate trichloroacetate, nickel myristate pentafluoropropionate and nickel 2-ethylhexanoate heptafluorobutyrate.

The nickel chelate compounds, which react with the alkyl aluminum alkoxides, are described in U.S. Pat. Nos. 3,424, 815 and 4,959,491, incorporated herein by reference. The nickel chelates include those having the formula

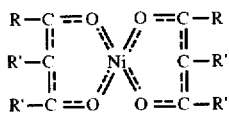

wherein R and R' independently are hydrogen, alkyl or aryl of up to 10 carbon atoms, or haloalkyl or haloaryl of up to 10 carbon atoms, with the proviso that the two R' groups of each chelating ligand together with the adjacent carbon atoms to which they are attached, can form a six-membered carbocyclic aromatic ring of up to 4 halogen substituents. The halogenated chelating ligand preferably has up to 15 carbon atoms and from 2 to 8 halogen substituents, but more preferably has up to 10 carbon atoms and from 3 to 6 halogen substituents. The halogen substituents of the chelating ligand are suitably fluorine, chlorine, bromine or iodine, wherein the R' groups together form a divalent radical in which the monoenol configuration is maintained as part of the aromatic ring;

The aluminum compound comprises an hydrocarbyl aluminum halide or a hydrocarbyl aluminum alkoxide. The hydrocarbyl group generally comprises 0, 1 or 2 hydrocarbyl groups each having from 1 to 20 carbon atoms, usually from 1 to 12 carbon atoms, the groups including alkyl, aryl, aralkyl, alkaryl, and cycloalkyl. The halide comprises 1 to 6 halides, such as fluoride, iodide, chloride, or bromide, preferably whichever is readily available, such as the chloride. Examples of the hydrocarbyl aluminum halides include AlCl3, ethylaluminum dichloride, ethylaluminum sesquichloride, dichloroethylaluminum, dichloroisobutylaluminum, chlorodiethylaluminum or their mixtures.

Suitable alkoxides can be 1 or 2 alkoxide groups whose alkyl segments are as defined above with respect to the alkyl groups attached to the aluminum.

Optionally, the catalyst may also contain a small amount of water which has the effect of increasing the rate of the catalytic dimerization. Generally, the amount of water employed will be an amount sufficient to increase the rate of the catalytic dimerization.

At the outlet of the reactor, the catalyst may be deactivated in known manner, for example, with ammonia and/or an aqueous sodium hydroxide solution and/or an aqueous sulfuric acid solution, or an organic acid/bicarbonate solution. The unconverted olefins and the alkanes, if any, are separated thereafter from the oligomers by distillation, or any other suitable procedure, such as extraction, and the like. Unreacted feedstock can be recycled back to the initial feedstock.

The present process and catalyst is especially useful for the dimerization of $C_6$–$C_{10}$ olefins having a high degree of linearity to ultimately produce high yields of $C_{13}$–$C_{21}$ branched primary alcohol compositions having an average number of branches per molecule of 0.9 to 2.0.

Conversion of the dimerized olefins to a primary alcohol composition is conveniently accomplished, for example, by hydroformylation, by oxidation and hydrolysis, by sulfation and hydration, by epoxidations and hydration, or the like. In hydroformylation, the dimerized olefins are converted to alkanols by reaction with carbon monoxide and hydrogen according to the Oxo process. Most commonly used is the "modified Oxo process", using a phosphine, phosphite, arsine or pyridine ligand modified cobalt or rhodium catalyst, as described in U.S. Pat. Nos. 3,231,621; 3,239,566; 3,239,569; 3,239,570; 3,239,571; 3,420,898; 3,440,291; 3,448,158; 3,448,157; 3,496,203; and 3,496,204; 3,501,515; and 3,527,818, the disclosures of which are incorporated herein by reference. Methods of production are also described in Kirk Othmer, "Encyclopedia of Chemical Technology" $3^{rd}$ Ed. vol 16, pages 637–653; "Monohydric Alcohols: Manufacture, Applications and Chemistry", E. J. Wickson, Ed. Am. Chem. Soc. 1981, incorporated herein by reference.

Hydroformylation is a term used in the art to denote the reaction of an olefin with CO and $H_2$ to produce an aldehyde/alcohol which has one more carbon atom then the reactant olefin. Frequently, in the art, the term hydroformylation is utilized to cover the aldehyde and the reduction to the alcohol step in total, i.e., hydroformylation refers to the production of alcohols from olefins via carbonylation and an aldehyde reduction process. As used herein, hydroformylation refers to the ultimate production of alcohols.

Illustrative catalysts include cobalt hydrocarbonyl catalyst, cobalt-phosphine ligand catalyst, and rhodium-phosphine ligand catalyst. The choice of catalysts determines the various reaction conditions imposed. These conditions can vary widely, depending upon the particular catalysts. For example, temperatures can range from about room temperatures to about 300° C. When cobalt carbonyl catalysts are used, which are also the ones typically used, temperatures will range from about 150° to about 250° C. One of ordinary skill in the art, by referring to the above-cited references, or any of the well-known literature on oxo alcohols can readily determine those conditions of temperature and pressure that will be needed to hydroformylat the dimerized olefins.

Typical reaction conditions, however, can be suitably carried out at moderate conditions. Temperatures in the range of 125° C. to 200° C. are recommended. Reaction pressures in the range of about 300 psig to about 1500 psig are typical, but lower or higher pressures may be selected. Ratios of catalyst to olefin ranging from 1:1000 to 1:1 are suitable. The ratio of hydrogen to carbon monoxide can vary widely, but is usually in the range of 1 to about 10, preferably from about 2 moles of hydrogen to one mole of carbon monoxide to favor the alcohol product.

The hydroformylation process can be carried out in the presence of an inert solvent, although it is not necessary. A variety of solvents can be applied such as ketones, e.g. acetone, methyl ethyl ketone, methyl isobutyl ketone, acetophenone and cyclohexanone; aromatic compounds such as benzene, toluene and the xylenes; halogenated aromatic compounds such as chlorobenzene and orthodichlorobenzene; halogenated paraffinic hydrocarbons such as methylene chloride and carbon tetrachloride; paraffins such as hexane, heptane, methylcyclohexane and isooctane and nitriles such as benzonitrile and acetonitrile.

With respect to the catalyst ligand, mention may be made of tertiary organo phosphines, such as trialkyl phosphines, triamyl phosphine, trihexyl phosphine, dimethyl ethyl phosphine, diamylethyl phosphine, tricyclopentyl(or hexyl) phosphine, diphenyl butyl phosphine, dipenyl benzyl phosphine, triethoxy phosphine, butyl diethyoxy phosphine, triphenyl phosphine, dimethyl phenyl phosphine, methyl diphenyl phosphine, dimethyl propyl phosphine, the tritolyl phosphines and the corresponding arsines and stibines. Included as bidentate-type ligands are tetramethyl diphosphinoethane, tetramethyl diphosphinopropane, tetraethyl diphosphinoethane, tetrabutyl diphosphinoethane, dimethyl diethyl diphosphinoethane, tetraphenyl diphosphinoethane, tetraperfluorophenyl diphosphinoethane, tetraphenyl diphosphinopropane, tetraphenyl diphosphinobutane, dimethyl diphenyl diphosphinoethane, diethyl diphenyl diphosphinopropane and tetratrolyl diphosphinoethane.

Examples of other suitable ligands are the phosphabicyclohydrocarbons, such as 9-hydrocarbyl-9-phosphabicyclononane in which the smallest P-containing ring contains at least 5 carbon atoms. Some examples include 9-aryl-9-phosphabicyclo|4.2.1|nonane, (di)alkyl-9-aryl -9-phosphabicyclo|4.2.1|nonane, 9-alkyl-9-phosphabicyclo|4.2.1|nonane, 9-cycloalkyl-9-phosphabicyclo|4.2.1|nonane, 9-cycloalkenyl -9-phosphabicyclo|4.2.1|nonane, and their |3.3.1| and |3.2.1| counterparts, as well as their triene counterparts.

The branched primary alcohol composition of the invention is suitable for the manufacture of anionic, nonionic, and cationic surfactants, preferably the former two, more preferably the anionic. Specifically, the branched primary alcohol composition of the invention can be used as the pecursor for the manufacture of anionic sulfates, including alcohol sulfates and oxylakylated alcohol sulfates, and nonionic oxyalkylated alcohols.

Any technique known for sulfating alcohols can be used herein. The primary alcohol composition may be directly sulfated, or first oxyalkylated followed by sulfatation. A preferred class of compositions comprises at least one anionic surfactant comprising the condensation product of the C8 to C36, particularly the C11 to C19 skeletally isomerized primary alcohol composition with or without ethylene oxide and/or propylene oxide, in which the number of ethoxy groups ranges from 3 to 12 and the ratio ethoxy/ propoxy is from 4 to 12, followed by sulfation.

The general class of anionic surfactants or alcohol ethoxysulfates can be characterized by the chemical formula:

R'—O—(CH2—CH2—O)x—SO3M(II)

wherein R' represents the skeletally isomerized olefin hydrophobe moiety, x represents the average number of oxyethylene groups per molecule and is in the range of from about 0 to about 12, and M is a cation selected from an alkali metal ion, an ammonium ion, and mixtures thereof. Of course, the surfactant can by oxyalkylated with any oxirane containing compound other than, in mixture with, or sequentially with ethylene oxide.

Sulfonation processes are described, for instance, in U.S. Pat. No. 3,462,525, issued Aug. 19, 1969 to Levinsky et. al., U.S. Pat. No. 3,428,654 issued Feb. 18, 1969 to Rubinfeld et. al., U.S. Pat. No. 3,420,875 issued Jan. 7, 1969 to DiSalvo et. al., U.S. Pat. No. 3,506,580 issued Apr. 14, 1970 to Rubinfeld et. al., U.S. Pat. No. 3,579,537 issued May 18, 1971 to Rubinfeld et. al., and U.S. Pat. No. 3,524,864 issued Aug. 18, 1970 to Rubinfeld, each incorporated herein by reference. Suitable sulfation procedures include sulfur trioxide (SO3) sulfation, chlorosulfonic acid (ClSO3H) sulfation and sulfamic acid (NH2SO3H) sulfation. When concentrated sulfuric acid is used to sulfate alcohols, the concentrated sulfuric acid is typically from about 75 percent by weight to about 100 percent by weight, preferably from about 85 percent by weight to about 98 percent by weight, in water. Suitable amounts of sulfuric acid are generally in the range of from about 0.3 mole to about 1.3 moles of sulfuric acid per mole alcohol, preferably from about 0.4 mole to about 1.0 mole of sulfuric acid per mole of alcohol.

A typical sulfur trioxide sulfation procedure includes contacting liquid alcohol or its ethoxylate and gaseous sulfur trioxide at about atmospheric pressure in the reaction zone of a falling film sulfator cooled by water at a temperature in the range of from about 25° C. to about 70° C. to yield the sulfuric acid ester of alcohol or its ethoxylate. The sulfuric acid ester of the alcohol or its ethoxylate then exits the falling film column and is neutralized with an alkali metal solution, e.g., sodium or potassium hydroxide, to form the alcohol sulfate salt or the alcohol ethoxysulfate salt.

Suitable oxyalkylated alcohols can be prepared by adding to the alcohol or mixture of alcohols to be oxyalkylated a calculated amount, e.g., from about 0.1 percent by weight to about 0.6 percent by weight, preferably from about 0.1 percent by weight to about 0.4 percent by weight, based on total alcohol, of a strong base, typically an alkali metal or alkaline earth metal hydroxide such as sodium hydroxide or potassium hydroxide, which serves as a catalyst for oxyalkylation. The resulting mixture is dried, as by vapor phase removal of any water present, and an amount of alkylene oxide calculated to provide from about 1 mole to about 12 moles of alkylene oxide per mole of alcohol is then introduced and the resulting mixture is allowed to react until the alkylene oxide is consumed, the course of the reaction being followed by the decrease in reaction pressure.

The oxyalkylation is typically conducted at elevated temperatures and pressures. Suitable reaction temperatures range from about 120° C. to about 220° C. with the range of from about 140° C. to about 160° C. being preferred. A suitable reaction pressure is achieved by introducing to the reaction vessel the required amount of alkylene oxide which has a high vapor pressure at the desired reaction temperature. For consideration of process safety, the partial pressure of the alkylene oxide reactant is preferably limited, for instance, to less than about 60 psia, and/or the reactant is preferably diluted with an inert gas such as nitrogen, for instance, to a vapor phase concentration of about 50 percent or less. The reaction can, however, be safely accomplished at greater alkylene oxide concentration, greater total pressure and greater partial pressure of alkyelene oxide if suitable precautions, known to the art, are taken to manage the risks of explosion. With respect to ethylene oxide, a total pressure of between about 40 and 110 psig, with an ethylene oxide partial pressure between about 15 and 60 psig, is particularly preferred, while a total pressure of between about 50 and 90 psig, with an ethylene oxide partial pressure between about 20 and 50 psig, is considered more preferred. The pressure serves as a measure of the degree of the reaction and the reaction is considered to be substantially complete when the pressure no longer decreases with time. It should be understood that the oxyalkylation procedure serves to introduce a desired average number of alkylene oxide units per mole of alcohol oxyalkylate. For example, treatment of an alcohol mixture with 3 moles of ethylene oxide per mole of alcohol serves to effect the ethoxylation of each alcohol molecule with an average of 3 ethylene oxide moieties per mole alcohol moiety, although a substantial proportion of alcohol moieties will become combined with more than 3 ethylene oxide moieties and an approximately equal proportion will have become combined with less than 3. In a typical ethoxylation product mixture, there is also a minor proportion of unreacted alcohol.

Other alkyene oxides can be used, such a proplyene oxide and butylene oxide. These may be added as a heteric mixture to the alcohol or sequentially to make a block stucture.

The sulfated primary alcohol composition of the invention can be used as surfactants in a wide variety of applications, including detergents such as granular laundry detergents, liquid laundry detergents, liquid dishwashing detergents; and in miscellaneous formulations such as general purpose cleaning agents, liquid soaps, shampoos and liquid scouring agents.

The sulfated primary alcohol composition of the invention find particular use in detergents, specifically laundry detergents. These are generally comprised of a number of components, besides the sulfated primary alcohol composition of the invention:

other surfactants of the ionic, nonionic, amphoteric or cationic type, builders (phosphates, zeolites),cobuilders (polycarboxylates), bleaching agents and their activators, foam controlling agents, enzymes, anti-greying agents, optical brighteners, and stabilizers.

Liquid laundry detergents generally comprise the same components as granular laundry detergents, but generally contain less of the inorganic builder component. Hydrotropes are often present in the liquid detergent formulations. General purpose cleaning agents may comprise other surfactants, builders, foam suppressing agents, hydrotropes and solubilizer alcohols.

In addition to surfactants, washing and cleaning agents may contain a large amount of builder salts in amounts up to 90% by weight, preferably between about 5 and 35% by weight, to intensify the cleaning action. Examples of common inorganic builders are phosphates, polyphosphates, alkali metal carbonates, silicates and sulfates. Examples of organic builders are polycarboxylates, aminocarboxylates such as ethylenediaminotetraacetates, nitrilotriacetates, hydroxycarboxylates, citrates, succinates and substituted and unsubstituted alkanedi- and polycarboxylic acids. Another type of builder, useful in granular laundry and built liquid laundry agents, includes various substantially water-insoluble materials which are capable of reducing the water hardness e.g. by ion exchange processes. In particular the complex sodium aluminosilicates, known as type A zeolites, are very useful for this purpose.

The formulations may also contain percompounds with a bleaching action, such as perborates, percarbonates, persulfates and organic peroxy acids. Formulations containing percompounds may also contain stabilizing agents, such as magnesium silicate, sodium ethylenediaminetetraacetate or sodium salts of phosphonic acids. In addition, bleach activators can be used to increase the efficiency of the inorganic persalts at lower washing temperatures. Particularly useful for this purpose are substituted carboxylic acid amides, e.g., tetraacetylethylenediamine, substituted carboxylic acids, e.g., isononyloxybenzenesulfonate and sodiumcyanamide.

Examples of suitable hydrotropic substances are alkali metal salts of benzene, toluene and xylene sulfonic acids; alkali metal salts of formic acid, citric and succinic acid, alkali metal chlorides, urea, mono-, di-, and triethanolamine. Examples of solubilizer alcohols are ethanol, isopropanol, mono- or polyethylene glycols, monopropylene glycol and etheralcohols.

Examples of foam control are high molecular weight fatty acid soaps, paraffinic hydrocarbons, and silicon containing defoamers. In particular hydrophobic silica particles are efficient foam control agents in these laundry detergent formulations.

Examples of known enzymes which are effective in laundry detergent agents are protease, amylase and lipase. Preference is given to the enzymes which have their optimum performance at the design conditions of the washing and cleaning agent.

A large number of fluorescent whiteners are described in the literature. For laundry washing formulations, the derivatives of diaminostilbene disulfonates and substituted distyrylbiphenyl are particularly suitable.

As antigreying agents, water soluble colloids of an organic nature are preferably used. Examples are water soluble polyanionic polymers such as polymers and copolymers of acrylic and maleic acid, cellulose derivatives such as carboxymethyl cellulose methyl- and hydroxyethylcellulose.

In addition to one or more of the aforementioned other surfactants and other detergent composition components, compositions according to the invention typically comprise one or more inert components. For instance, the balance of liquid detergent composition is typically an inert solvent or diluent, most commonly water. Powdered or granular detergent compositions typically contain quantities of inert filler or carrier materials.

A further understanding of the invention can be had from the following nonlimiting examples.

EXAMPLE 1

This example demonstrates the manufacture of a dimerized monobranched $C_{12}$–$C_{15}$ alcohol from internal olefins using a nickel chelate catalyst.

A flask was charged with 2268.7 grams of a $C_6$–$C_8$ internal olefins having some 4, 5, 9, and 10 carbon olefins, and distilled using an 11 plate Oldershaw distillation column with a swinging bucket reflux splitter condensor, a dry ice chilled trap, and a nitrogen blanket. After about 37 hours of distillation, those cuts distilling up to 138° C. in the pot and 125° C. at the head were collected for a total amount of about 1200 grams. These cuts represent the light ends of the olefin, $C_{4-8}$.

The 1200 grams of the $C_{4-8}$ olefin feed was dimerized by the following method.

The 1200 grams of the olefin was poured into a 5l round bottom flask equipped with a condensor, a dry ice condensor, a thermocouple, a water bath, and a nitrogen blanket.

About 19.74 g of dried nickel hexafluoroacetoacetyl acetonate (nickel catalyst) and 53.76 g of an 11/89 wt. % solution of diethylaluminum ethoxide in cyclohexane (aluminum solution) were added sequentially and stirred into the olefin. The reaction mixture was heated up to 35° C. for 6 and ½ hours, after which 14.38 more grams of the aluminum solution were added, heated up to 37° C. for an additional 2 hours, after which 4.0 more grams of the nickel catalyst and 13.75 g of the aluminum solution were added, heated up to 35° C. to 37° C. for about another 10 hours, after which 15.55 more grams of the aluminum solution were added followed by heating for another 4 hours, after which 4 more grams of the nickel catalyst and 14.4 more grams of the aluminum solution were added, followed by heating for another 5 hours, after which 21.0 more grams of the aluminum solution and 5.0 grams of the nickel catalyst were added, followed by heating for another 3 hours, after which 4.18 grams of the nickel catalyst and 20.1 more grams of the aluminum solution were added.

Subsequently, the reaction product in the flask was quenched with 100 g of citric acid and about 22 g of a sodium bicarbonate solution per quart of water, and filtered.

The dimerized $C_{4-8}$ olefin was then subjected to further distillation to obtain cuts having predominantly $C_{13-14}$ olefins. The distillation was conducted as above, except with a 10 plate Oddershaw column, and those cuts distilling at 169° C. to 194° C. in the pot and 129° C. to 155° C. at the head, at 47 to 48 mmHg vacuum, were collected, for a total of 188.05 grams.

150 grams of this batch was then subjected to hydroformylation in a 500 ml autoclave, using the modified oxo process. The 150 grams of the dimerized olefin were reacted with hydrogen and carbon monoxide at a $H_2/CO$ ratio of 2, in the presence of a phosphine modified cobalt catalyst and potassium hydroxide in ethanol at a temperature of up to about 180° C., a stirring speed of 1250 rpm, and a pressure of about 1000 psig, for about 20 hours. After completion of the reaction, the product was cooled to 60° C.

The hydroformylated dimerized alcohols were subjected to further flash volatilization to separate out any unconverted olefin and paraffins. Those cuts distilling at 182° C. to 250° C. in the pot and 99° C. to 112° C. at the head were collected, and neutralized with sodium borohydride. The distillate cuts, totaling 300 ml, were added to a round bottom flask, stirred and heated to 50° C., to which 0.6 grams of the sodium borohydride were added and reacted for about 2 hours, after which 0.6 more grams of the sodium borohydride were added and reacted for another 1.5 hours at 75°–80° C., and then reacted for another 2 and ½ hours at 98°–100° C. The solution was left to cool, transferred to a 500 ml flask, washed by shaking with 70° C. deionized water under ventilation, let stand, to which was added 20 ml of ethyl ether, shaken, and separated. The water phase was drained and the process repeated another two times using ethyl ether. After washing, about 10 grams of sodium sulfate was added to the alcohol, shook, and then let stand. The product was filtered, the liquid transferred to a 250 ml flask, and then subjected to further distillation to rid the solution of the light ends. The distillates obtained up to 102° C. in the pot and 163° C. at the head were discarded, and 82.91 ml of the contents in the pot were recovered. These contents were monobranched $C_{12-16}$ alcohols, having about 42% $C_{14}$, 44% $C_{15}$, and about 8% $C_{16}$ alcohols as determined by GCMS, and were subjected to analytical testing and further reaction for making the sulfates.

EXAMPLE 2

This example demonstrates the preparation of a $C_{13-17}$ dimerized monobranched alcohol from internal olefins using a nickel carboxylate catalyst.

The same procedure as used in Example 1 above was followed with the following noted exceptions. The amount of $C_{4-10}$ internal olefins distilled was 2427.7 grams. 712.5 grams of distillate boiling at 120° to 154° C. in the pot and 89° C. to 129° C. at the head were collected. The reflux was set at 5 seconds on, and 7 seconds off. The distillate cuts were predominantly $C_{6-9}$ carbon chain internal olefins. 702.6 grams of these olefins were dimerized in a 2 liter flask using 0.493 g of nickel 2-ethylhexanoate-trifluoroacetate in 5 ml of cyclohexane and 12 ml of a 1 molar solution of ethylaluminum dichloride in hexane, (first batch of catalyst) as the dimerization catalysts injected into the olefin. The contents of the flask were heated to 35°–38° C. on average throughout the course of the reaction. After about 3 hours of heat, a second batch catalyst in the same amount was added. After another hour of heat, a third batch of catalyst in the same amount was added, and after another hour and 15 minutes, a fourth batch of catalyst in the same amount was added. After about 6 and ½ hours, the fifth batch of catalyst in the same amount was added, and after about another 7 hours of heat, another catalyst batch in the same amount was added, and finally after another 1 and ½ hours, the final catalyst batch in the same amount was added. The contents of the flask were heated for another hour.

To neutralize the dimerization catalyst, 22 g of sodium bicarbonate in 250 g of deionized water was added to 100 g of citric acid in 100 grams of deionized water, to which was added more water to make a 1 liter batch. The dimerized olefins were poured into a 2 liter separation funnel with ½ liter of the citric acid/bicarbonate solution, shook and vented, separated, and repeated. The neutralized dimerized solution was dried with sodium sulfate as above.

As in example 1, the olefins were further distilled to acquire $C_{6-9}$ olefins. Those distillate cuts boiling at 157° C. in the pot and 125° C. at the head at 41 mmHg, and those boiling at 139° C. to 164° C. in the pot at 14 mmHg, and those boiling at from 179° C. to 240° C. in the pot at 13 mmHg were collected for a total of 231.95 grams of distillate.

The dimerized distillate was hydroformylated as above and flash distilled at about 4–5 mmHg. 1.39 g of sodium borohydride was added to 211.48 g of the distilled alcohol, heated to 50° C. for 1 hour, after which another 1.3 g of sodium borohydride was added and heated to 90° C. for four hours and cooled.

The product was washed as above, and redistilled with those distillate cuts boiling at 141.5° to 240° C. in the pot and 100° C. to 104° C. at the head being collected at 3 mmHg. The monobranched $C_{13-17}$ alcohols, having about 25% $C_{14}$, 40% $C_{15}$, and 25% $C_{16}$ alcohols, as determined by GCMS, were collected and subjected to analytical testing and sulfation as described below.

EXAMPLE 3

This example demonstrates the preparation of a $C_{13,15,17}$ dimerized monobranched alcohols from alpha olefins.

In this example, a mixture of 600 g NEODENE® 6 α-olefin, a $C_6$ olefin, and 800 g of NEODENE® 8 α-olefin, a $C_8$ olefin, containing 5.32 g of ethylaluminum dichloride, were added to a 5 liter flask. The same procedure as used in example 1 was followed with the following differences. A solution of 7.9 g of the nickel 2-ethylhexanoate-trifluoroacetate in 6.35 g of cyclohexane (the nickel solution) was added and heated. The flask was maintained at from 33° C. to 38° C. throughout the course of the reaction. Another 7.6 ml of the aluminum solution as prepared in example 2 and 5 ml of the nickel solution were injected into the reaction flask after about 8 hours of heating.

About 1.5 liters of the sodium citrate neutralizing solution was used to neutralize the dimerized olefins, separated, and again repeated. The dimerized product was distilled, with the cuts distilling at 149° C. to 160° C. in the pot and 137° C. to 148° C. at the head, at 60 mmHg, 120° C. to 133° C. in the pot and 110° to 122° C. at the head at 9 mmHg, and 127° to 149° C. in the pot and 118° C. to 145° C. at the head at 10 mmHg being collected for a total of 786.4 g.

730 g of these dimerized olefins were hydroformylated in a 1 gallon autoclave, reacted at temperatures up to about 240° C. at pressures up to 1145 psig.

809 g of the hydroformylated olefins were treated with 6.5 g of sodium borohydride, as above, followed by another addition of 6.5 g of sodium borohydride and heating, and a third addition of 4.95 g followed by 6 hours of heating at up to 99° C.

The treated hydroformylated olefins were washed as in example 1, filtered, and distilled with those cuts distilling at 152° to 181° C. in the pot and 137° to 172° C. at the head at 6 mmHg being collected for a total of 495 g of $C_{13}$, $C_{15}$, and $C_{17}$ monobranched alcohols. The sample was analytically tested and sulfated as described below.

EXAMPLE 4

Each of the monobranched alcohol compositions described in examples 1–3 were sulfated by adding dropwise chlorosulfonic acid to the alcohol composition. Specifically, the alcohol compositions were sparged for 2–3 hours with nitrogen in a flask, after which about 1 ml of methylene chloride per gram of the alcohol composition was added. The chlorosulfonic acid was added dropwise to the alcohol composition in the flask for about 25 minutes, while maintaining the temperature at about 30°–35° C. More methylene chloride was added if the solution became to viscous. The solution was then sparged with nitrogen for 2–3 minutes to facilitate removal of HCl, after which it was added slowly to a chilled 50% sodium hydroxide in 3A alcohol solution to neutralize the alcohol composition. If the pH was below 8, more of the basic solution was added, until the pH was adjusted to between 8–9. If too acidic, a 50% solution of $H_2SO_4$ was added to adjust the pH. The solution was stirred for another hour, and the pH adjusted accordingly within the stated range. Methylene chloride was removed by a rotary evaporator under reduced pressure at about 40° C. under a nitrogen sparge.

The alcohol compositions of examples 1–3 were subsequently tested for amount, type, and location of branching using the JSME NMR method described herein. For a determination of quaternary carbon atoms, the quat only JSME NMR technique described herein was used. These results are reported in Table I below. The average carbon number was determined by GCMS. The sulfated primary alcohol samples were also tested for biodegradability, the results of which are reported in Table II; and detergency, the results of which are reported in Table III. The examples reported in the tables are arranged by order of chain length for ease of viewing, and identified as 4—indicating the sulfate of a corresponding example number. Each of these tests were conducted in accordance with the procedures specified above. As a comparison example, Neodol® 45-S was tested for branching, biodegradability, and detergency. Neodol® 45-S was used as the comparison because it is the current commercial primary alcohol composition, which when sulfated, is currently used in detergents and is known for its ready biodegradability. Also as a comparison, a sulfated Exxal-13S alcohol believed to have a predominance of $C_{13}$ alcohols and derived from propylene oligomerization through acid catalysis and then subjected to hydroformylation using an oxo process, was subjected to biodegradation testing. EXXAL® 13 is reported to have about 3–4 methyl branches per tridecyl-alcohol molecule.

TABLE I

| NMR Structural Characterization | | | | |
|---|---|---|---|---|
| Analysis | Ex 1, a $C_{12-15}$ alcohol | Ex 2, a $C_{13-15}$ alcohol* | Ex 3, a $C_{13,15,17}$ alcohol | Neodol® 45, a $C_{14-15}$ alcohol |
| Average Carbon Number | 14.5 | 15.5 | 16.8 | 14.7 |
| Average Branches per Chain | 1.0 | 1.4 | 1.5 | 0.3 |
| Branch Position Relative To Hydroxyl Carbon | | | | |
| % @ C4 position and further, including no branching | 83.7 | 85 | 83.4 | 81.5 |
| % @ C3 position | 4.7 | 3 | 2.7 | 0.0 |
| % methyl @ C2 position | 6.4 | 6 | 7.4 | 7.4 |
| % ethyl @ C2 position | 1.6 | 2 | 6 | 2.7 |
| % propyl and longer @ C2 position | 3.6 | 4 | 4.1 | 8.4 |

TABLE I-continued

| NMR Structural Characterization | | | | |
|---|---|---|---|---|
| Analysis | Ex 1, a $C_{12-15}$ alcohol | Ex 2, a $C_{13-15}$ alcohol* | Ex 3, a $C_{13,15,17}$ alcohol | Neodol® 45, a $C_{14-15}$ alcohol |
| Types Of Branching | | | | |
| % Butyl or longer | 52.2 | 28 | | |
| % Propyl | 17.5 | 12 | 66.7** | 88.8** |
| % ethyl | 16 | 23 | 12.9 | 3.1 |
| % methyl | 14.2 | 37 | 20.4 | 8.1 |
| Quaternary Carbons Detected | na | none | na | none |

*Approximately 21% of the branching was conjugated with methyl branches on adjacent carbons in the chain.
**Includes propyl and butyl branching.

The results indicate that the dimerized alcohols look very much the same as NEODOL® alcohols with respect to the branch positions, according to the NMR analysis. Specifically, very few branches are located at the $C_{2-4}$ carbon positions. Since the average number of branches of the dimerized alcohols far exceeds that of NEODOL® alcohols, the center of the molecule carbon backbone must be where the predominant number of branches are situated, i.e. an excess of 80%. By center is meant the $C_4$ position inward from each end of the molecule.

Also noteworthy is the higher percentage of ethyl branches on the dimerized alcohols of the invention as compared to the relatively few ethyl branches found in the NEODOL® alcohol.

TABLE II

| % Biodegradation of Dimerized Alcohol Sulfates | | | | |
|---|---|---|---|---|
| Example No. | 5-day | 10-day | 15-day | 28-day |
| 4–1 | 19 | 43 | 61 | 68 |
| 4–2 | 23 | 39 | 65 | 73 |
| 4–3 | 28 | 35 | 60 | 64 |
| A sulfated Neodol® $C_{14-15}$ alcohol | 40 | 64 | 71 | 75 |
| A sulfated Exxal 13-S | 4 | 12 | 21 | 40 |

The OECD 301 D biodegradation results indicate that each of the sulfated primary alcohol compositions of the invention readily biodegraded, as did the Neodol® sulfated alcohol. The sulfated Exxal® alcohol only poorly biodegraded.

TABLE III

| Multisebum Detergencies of Dimerized Alcohol Sulfates | | |
|---|---|---|
| Example No. | 50° F. | 90° F. |
| 4–1 | 27 | 31 |
| 4–2 | 21 | 31 |
| 4–3 | 15 | 25 |
| A sulfated Neodol® $C_{14-15}$ alcohol | 11 | 29 |

$LSD_{95}$ is 5.0 at both temperatures.

The detergency evaluations indicate that the dimerized alcohols of the invention have superior or equal cold water detergency as compared to the conventional NEODOL® sulfated alcohol.

What we claim is:

1. A process for the manufacture of a branched $C_{13}$–$C_{21}$ alcohol composition having an average number of branches ranging from 0.9 to 2.0, comprising:
   a) dimerizing, in the presence of a homogeneous dimerization catalyst under dimerization conditions, an olefin feed comprised of $C_6$–$C_{10}$ olefins, to obtain $C_{12}$–$C_{20}$ olefins; and
   b) converting said $C_{12}$–$C_{20}$ olefins to alcohols.

2. The process of claim 1, wherein olefin feed comprises at least 85% linear olefins.

3. The process of claim 2, wherein the olefin feed comprises at least 90% linear olefins.

4. The process of claim 3, wherein the olefin feed comprises at least 95 wt % of linear olefins.

5. The process of claim 2, wherein at least 85% of the olefin feed comprises $C_6$–$C_{10}$ olefins.

6. The process of claim 1, wherein greater than 50 wt. % of the olefin feed comprises internal olefins.

7. The process of claim 1, wherein said conversion is accomplished by hydroformylating the olefins to alcohols.

8. The process of claim 1, wherein said process of dimerizing the olefin feed is a one-step dimerization process.

9. The process of claim 8, wherein said $C_6$–$C_{10}$ olefins are obtained by the Fisher Tropsch process.

10. The process of claim 8, wherein said conversion is accomplished by hydroformylating the olefins to alcohols.

11. The process of claim 10, wherein said homogenous dimerization catalyst comprises a combination of a nickel carboxylate with an alkyl aluminum halide, or a nickel chelate with an alkyl aluminum alkoxide.

12. The process of claim 11, wherein said halide comprises a chloride, and said carboxylate comprises one or two alkyl groups having from 5 to 20 carbon atoms.

13. The process of claim 12, wherein one of the alkyl groups comprises a halogenoalkyl group having 1 to 3 carbon atoms.

14. The process of claim 11, wherein said nickel chelate is represented by the formula:

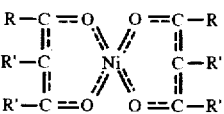

wherein R and R' independently are hydrogen, alkyl or aryl of up to 10 carbon atoms, or haloalkyl or haloaryl of up to 10 carbon atoms.

15. A branched alcohol composition comprising the reaction product of an olefin feed comprising $C_6$–$C_{10}$ linear olefins dimerized to a $C_{12}$–$C_{20}$ olefins composition followed by conversion to an alcohol composition having an average number of branches ranging from 0.9 to 2.0 per molecule.

16. The alcohol composition of claim 15, wherein said composition has less than 25% branching at the $C_2$, $C_3$, and isopropyl terminal carbon positions relative to the hydroxyl bearing carbon atom.

17. The alcohol composition of claim 15, wherein said alcohol composition has less than 25% terminal isopropyl branching, relative to the hydroxyl carbon.

18. The alcohol composition of claim 15, wherein said alcohol composition has no isopropyl terminal branching.

19. The alcohol composition of claim 15, the average number of branches ranges from about 1 to 1.8.

20. The alcohol composition of claim 19, wherein the average number of branches ranges from greater than 1 to 1.8.

21. The alcohol composition of claim 15, wherein the alcohol compositions contain $C_1$–$C_3$ types of branches located at one or both of the dimerized carbon atoms.

22. The alcohol composition of claim 15, wherein at least 5% of the alcohol composition comprises conjugated branches.

23. The alcohol composition of claim 15, wherein the alcohol composition contains from 10 to 30% ethyl types of branches.

* * * * *